United States Patent
Biber et al.

(10) Patent No.: US 9,958,517 B2
(45) Date of Patent: May 1, 2018

(54) SHOULDER COIL HAVING A FLEXIBLE TOP PART AND/OR A MOUNTING-DEPENDENT ELEMENT SELECTION

(75) Inventors: Stephan Biber, Frauenaurach (DE); Rainer Kurth, Erlangen (DE); Stephan Zink, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1500 days.

(21) Appl. No.: 13/484,183

(22) Filed: May 30, 2012

(65) Prior Publication Data
US 2013/0137970 A1 May 30, 2013

(30) Foreign Application Priority Data
May 31, 2011 (DE) .................. 10 2011 076 824

(51) Int. Cl.
| | | |
|---|---|---|
| *A61B 5/05* | (2006.01) | |
| *G01R 33/34* | (2006.01) | |
| *G01R 33/3415* | (2006.01) | |
| *A61B 5/055* | (2006.01) | |
| *A61B 5/00* | (2006.01) | |

(52) U.S. Cl.
CPC ... *G01R 33/34084* (2013.01); *G01R 33/3415* (2013.01); *A61B 5/055* (2013.01); *A61B 5/4576* (2013.01)

(58) Field of Classification Search
USPC .......... 600/407, 410, 422; 324/306–309, 318
See application file for complete search history.

(56) References Cited

U.S. PATENT DOCUMENTS

| | | | |
|---|---|---|---|
| 5,136,244 A | 8/1992 | Jones et al. | |
| 6,943,551 B2 | 9/2005 | Eberler et al. | |
| 7,031,763 B1* | 4/2006 | Zhang ........................... | 600/422 |
| 7,466,130 B1* | 12/2008 | Votruba et al. ............... | 324/318 |
| 2005/0107686 A1* | 5/2005 | Chan .................. | G01R 33/3415 |
| | | | 600/422 |
| 2006/0267587 A1 | 11/2006 | Iwadate et al. | |
| 2008/0007250 A1* | 1/2008 | Wiggins ................. | A61B 5/055 |
| | | | 324/200 |
| 2010/0280360 A1 | 11/2010 | Biber et al. | |

FOREIGN PATENT DOCUMENTS

| | | |
|---|---|---|
| CN | 1311444 A | 9/2001 |
| CN | 1896763 A | 1/2007 |
| CN | 101452065 A | 6/2009 |
| CN | 101874731 A | 11/2010 |
| DE | 103 14 215 B4 | 11/2006 |
| WO | WO 2007/048032 A1 | 4/2007 |

OTHER PUBLICATIONS

German Office Action dated Mar. 1, 2012 for corresponding German Patent Application No. DE 10 2011 076 824.6 with English translation.
Chinese Office Action for Chinese Patent Application No. 201210176531.7, dated Aug. 3, 2015 with English Translation.

* cited by examiner

*Primary Examiner* — Joel F Brutus
(74) *Attorney, Agent, or Firm* — Lempia Sumerfield Katz LLC

(57) ABSTRACT

A shoulder coil for a magnetic resonance imaging device includes a bottom part and one or more top part elements that may be moved relative to the bottom part. The one or more top elements each have at least one coil therein.

16 Claims, 3 Drawing Sheets

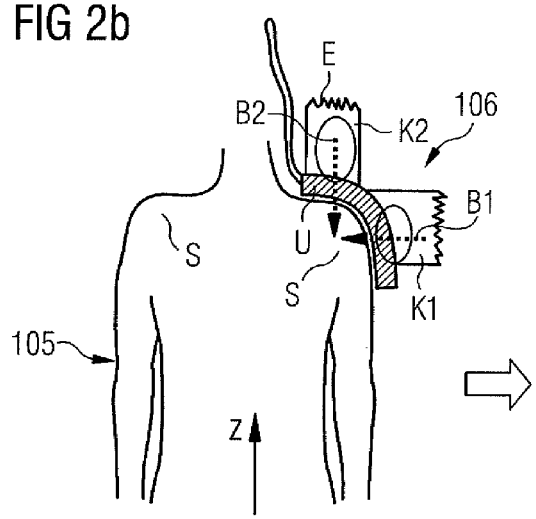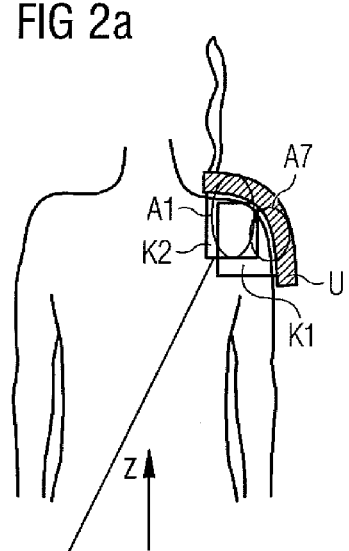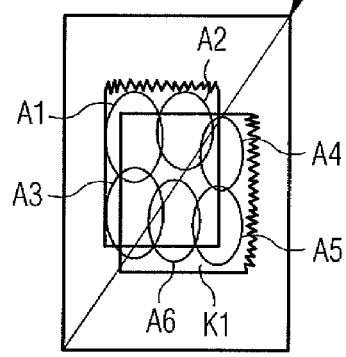

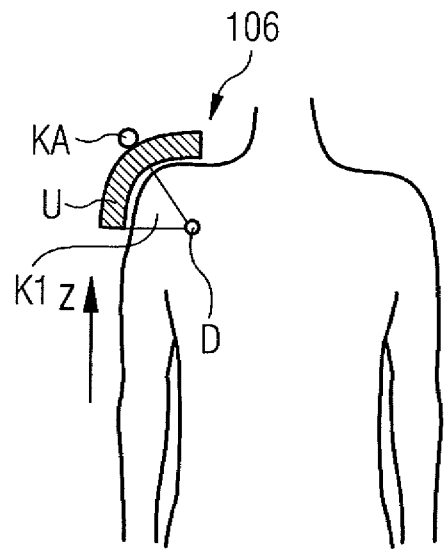
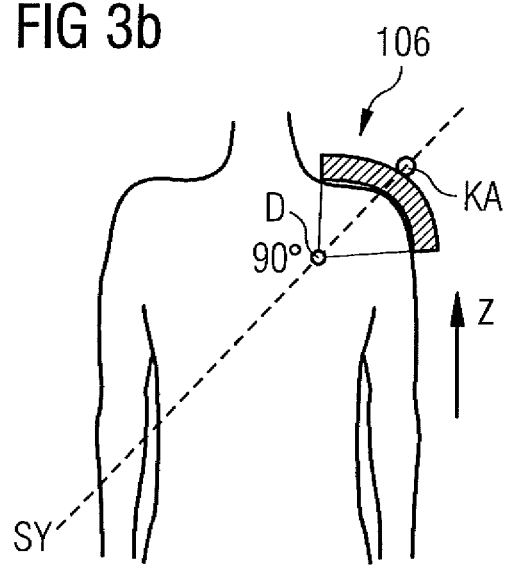

US 9,958,517 B2

SHOULDER COIL HAVING A FLEXIBLE TOP PART AND/OR A MOUNTING-DEPENDENT ELEMENT SELECTION

This application claims the benefit of DE 10 2011 076 824.6, filed on May 31, 2011.

BACKGROUND

The present embodiments relate to a magnetic resonance tomography (MRT) local coil for an MRT system.

Magnetic resonance imaging devices for examining objects or patients by magnetic resonance imaging (MRT, MRI) are described by way of example in DE10314215B4.

In MR imaging, images with a high signal-to-noise ratio (SNR) may be recorded using local coils (e.g., coils). The local coils are antenna systems that are provided in the immediate vicinity above (anterior) or below (posterior) the patient.

During an MR measurement, the excited cores induce a voltage in the individual antennae of the local coil. The induced voltage is amplified by a low-noise amplifier (e.g., LNA, preamp) and is forwarded in a wired manner to the electronic receiving device. High-field units (e.g., 1.5 T to 12 T and more) are used to improve the signal-to-noise ratio even in the case of high resolution images.

The SNR of an image is significant in many clinical MR applications. The SNR is determined by the local coil (e.g., with antenna and active amplifiers), for example, by the losses in the antenna elements themselves. Very small antennae allow a very high SNR close to the antenna. For this reason and owing to the possibility of accelerated measurement by way of k-space subsampling (e.g., parallel imaging, SENSE, GRAPPA), there is an interest in high-channel (e.g., with a large number of channels), very dense antenna arrays having individual elements that may have a completely different orientation relative to the sending field. In addition to the SNR, the simple practicability of the local coil is a feature that may be taken into account. An advantageous arrangement of local coil elements together with a workflow-optimized mechanical design are important for simultaneous optimization of SNR and workflow.

Local coils exist in many forms, often dedicated to specific regions of the body (e.g., head, heart, prostate, knee, ankle, shoulder joint).

SUMMARY

Local coils for use on the shoulder joint may have the following problems. A shoulder joint is located deep in the body and therefore may not be accessed from all sides. The variation in patient anatomy is great in the region of the shoulder. Owing to the asymmetrical position of the shoulder on the body, the local coil may not surround the joint completely. As a result, the SNR and brightness characteristic is asymmetrical in all spatial directions. The attainable SNR is also lower compared with a thick knee joint, which is located similarly deep in the body, because the region of interest (ROI) may not be encompassed by coil elements from all sides.

The present embodiments may obviate one or more of the drawbacks or limitations in the related art. For example, a local coil for a shoulder is optimized for a magnetic resonance imaging device.

BRIEF DESCRIPTION OF THE DRAWINGS

FIG. 2a shows a plan view of one embodiment of a shoulder coil in an open position of top part elements of the shoulder coil;

FIG. 2b shows a plan view of one embodiment of a shoulder coil in a closed position of the top elements of the shoulder coil;

FIG. 2c shows an enlarged cross-sectional view of a detail of one embodiment of a shoulder coil;

FIG. 3a shows a plan view of one embodiment of a shoulder coil with top part elements above a right shoulder of a patient; and FIG. 3b shows a plan view of one embodiment of a shoulder coil with top part elements above a left shoulder of a patient.

DETAILED DESCRIPTION OF THE DRAWINGS

Figure 1:
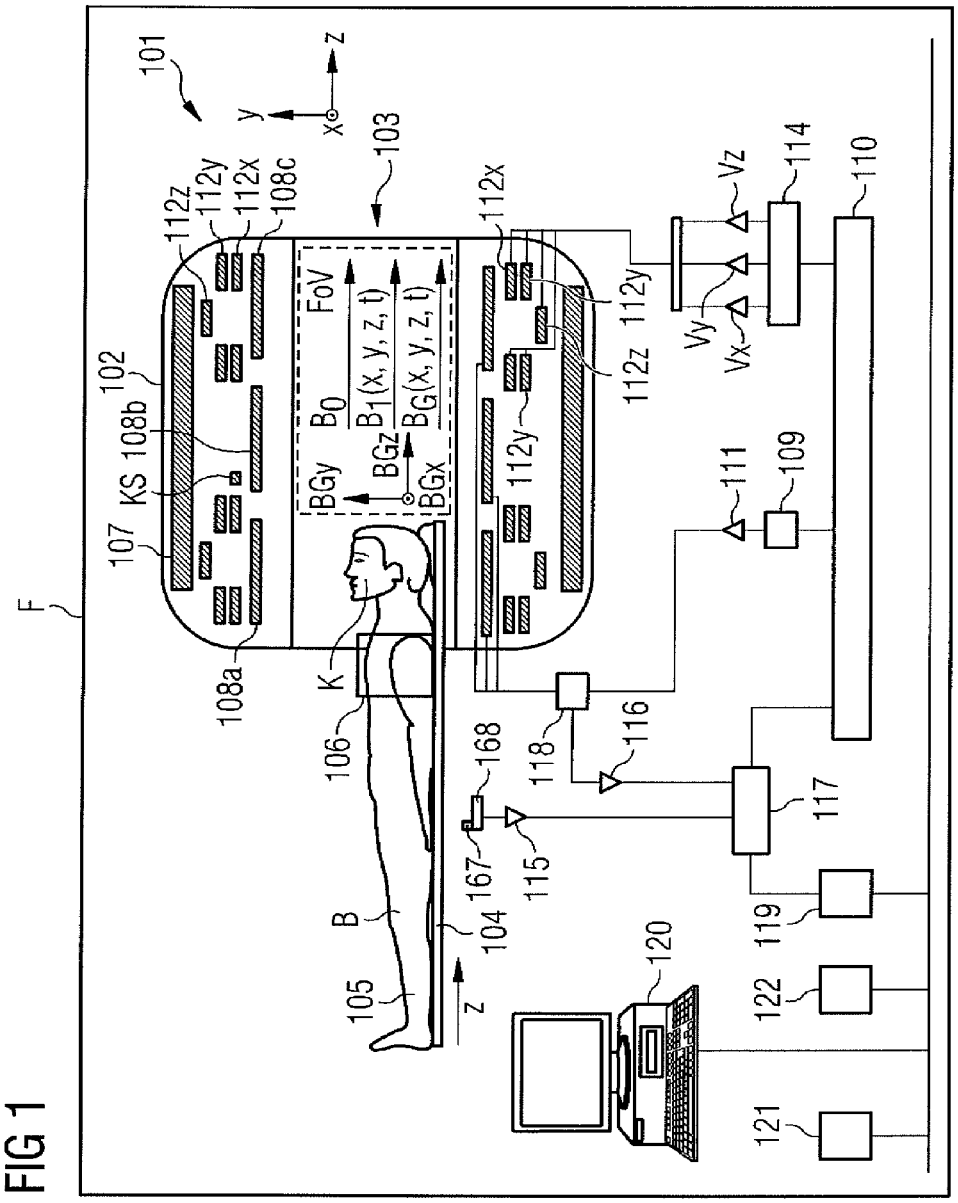
FIG. 1 shows an magnetic resonance tomography (MRT) system.

FIG. 1 shows a magnetic resonance tomography (MRT) device 101 (e.g., magnetic resonance imaging (MRI) device; located in a shielded room or Faraday cage F) having a whole-body coil 102 with a, for example, tubular space 103. An examination table 104 with a body, for example, of an object to be examined 105 (e.g., a patient; with or without local coil arrangement 106) may be moved in the tubular space in the direction of arrow z to generate images of the patient 105 by way of an imaging method. Arranged on the patient in FIG. 1 (e.g., secured by a belt) is a local coil arrangement 106 (e.g., secured by the same or another belt), with which in a local region (e.g., field of view (FoV)) of the MRT device 101, images of a section of the body 105 may be generated in the FoV. Signals of the local coil arrangement 106 may be evaluated (e.g., converted into images, stored or displayed) by an evaluator (e.g., including elements 168, 115, 117, 119, 120, 121) of the MRT device 101. The evaluator of the MRT device 101 may be connected to the local coil arrangement 106, for example, via coaxial cable or via radio (e.g., including element 167).

To examine a body 105 (e.g., the object to be examined or the patient) using the MRT 101 device for magnetic resonance imaging, different magnetic fields that are coordinated with each other as precisely as possible in terms of temporal and physical characteristics, are radiated onto the body 105. A strong magnet (e.g., a cryomagnet 107) in a measuring cabin having a, for example, tunnel-shaped opening 103, produces a static strong main magnetic field $B_0$. The value of the static strong main magnetic field $B_0$ is, for example, 0.2 Tesla to 3 Tesla or more. The body 105 to be examined, positioned on the examination table 104, is moved into a region of the main magnetic field B0 that is roughly homogenous in the FoV. The nuclear spin of atomic nuclei in the body 105 is excited by way of magnetic high frequency excitation pulses $B1(x, y, z, t)$ that are radiated via a high frequency antenna (and/or optionally, a local coil arrangement) shown in FIG. 1 in simplified form as a body coil 108 (e.g., a multi-part body coil 108a, 108b, 108c). High frequency excitation pulses are produced, for example, by a pulse-generating unit 109 that is controlled by a pulse sequence control unit 110. Following amplification by way of a high frequency amplifier 111, the high frequency excitation pulses are conveyed to the high frequency antenna 108. The high frequency system illustrated in FIG. 1 is schematically shown. In other embodiments, more than one pulse-generating unit 109, more than one high frequency amplifier 111, and a plurality of high frequency antennae 108 a, b, c are used in a magnetic resonance device 101.

The magnetic resonance device 101 also includes gradient coils $112x$, $112y$, $112z$, with which magnetic gradient fields for selective layer excitation and for spatial encoding of the measuring signal are radiated during a measurement. The gradient coils 112x, 112y, 112z are controlled by a gradient coil control unit 114 that, like the pulse-generating unit 109, is also connected to the pulse sequence control unit 110.

Signals emitted by the excited nuclear spin (e.g., the atomic nuclei in the object to be examined) are received by the body coil 108 and/or at least one local coil arrangement 106, amplified by associated high frequency amplifiers 116, and processed further and digitized by a receiving unit 117. The recorded measuring data are digitized and stored in a k-space matrix as complex numerical values. An associated MR image may be reconstructed from the k-space matrix occupied by values using a multi-dimensional Fourier transformation.

For a coil that may be operated in both transmitting and receiving modes (e.g., the body coil 108 or the local coil 106), correct signal forwarding is regulated by a transceiver switch 118 connected upstream.

An image processing unit 119 produces an image from the measuring data that is displayed to a user via a control panel 120 and/or is stored in a memory unit 121. A central computer unit 122 controls the individual unit components.

In MR imaging, images with a high signal-to-noise ratio (SNR) may be recorded using local coil arrangements (e.g., coils, local coils). The local coil arrangements are antenna systems that are provided in the immediate vicinity above (anterior), below (posterior), on, or in the body 105.

During an MR measurement, the excited cores induce a voltage in the individual antennae of the local coil. The induced voltage is amplified by a low-noise amplifier (e.g., LNA, preamp) and is forwarded to the electronic receiving device. High-field units (e.g., 1.5 T and more) are used to improve the signal-to-noise ratio even in the case of high resolution images. If it is possible to connect more individual antennae to an MR receiving system than there are receivers available, a switch matrix (e.g., an RCCS here), for example, is fitted between receiving antennae and receivers. This routes the instantaneously active receiving channels (e.g., receiving channels that are located precisely in the field of view of the magnet) to the available receivers. More coil elements than there are receivers available may be connected, since in the case of whole body coverage, only the coils that are located in the FoV or the homogeneity volume of the magnet are to be read out.

In one embodiment, an antenna system that may include, for example, one antenna element or an array coil of a plurality of antenna elements (e.g., coil elements) may be designated a local coil arrangement 106. These individual antenna elements are configured, for example, as loop antennae (e.g., loops), butterfly, flex coils or saddle coils. A local coil arrangement includes, for example, coil elements, an amplifier, further electronic devices (e.g., baluns), a housing, supports and may include a cable with connectors, by which the local coil arrangement is connected to the MRT device 101. A receiver 168 provided on the MRT device 101 filters and digitizes a signal received from a local coil 106, for example, via radio and passes the data to a digital signal processing device that may derive an image or a spectrum from the data obtained by a measurement. The digital signal processing device makes the image or the spectrum available to the user, for example, for subsequent diagnosis by the user and/or storage.

Details of exemplary embodiments of MRT shoulder local coils 106 are described in more detail below with reference to FIGS. 2a-2c and 3a-3b.

An object to be examined (e.g., the patient 105) is to be examined lying on the examination table 104 in the MRT 101 using the local coil 106 on at least one shoulder S of the patient 105.

In exemplary embodiments of the MRT shoulder local coils 106 according to FIGS. 2a-2c, 3a-3b, a combination of a fixed shoulder coil bottom part U and flexibly moldable/placeable shoulder coil top part elements K1, K2 (e.g., elements that may be hinged into a position according to FIGS. 3a-3b in the y-direction/vertically above the shoulder of the patient) is shown. The shoulder coil top part elements K1, K2 are shown in the form of hinged elements K1, K2 each having at least one coil A1, A2 therein (e.g., with variable choice of top part elements K1, K2).

A shoulder coil 106 is placed, for example, in a position on the examination table 104, at which a shoulder S of the patient 105 may be roughly positioned and, more precisely, using flexible hinged elements (or top part elements) K1, K2 according to FIG. 2b (e.g., opened away from the shoulder position and/or from the bottom part U of the shoulder coil 106 resting on the examination table 104). The patient 105 lies on the examination table 104 in such a way that one shoulder S rests on the bottom part U of the shoulder coil 106, and the flexible hinged elements/top part elements K1, K2 are hinged upwards (y) into a position according to FIG. 2a, 2c, 3a or 3b (e.g., completely/partially) above one shoulder S.

The flexible top part elements K1, K2 (or hinged elements K1, K2) allow the shoulder local coil 106 to be adjusted to different patient anatomies, since the flexible top part elements K1, K2 may be flexibly moved/hinged above the shoulder S of the patient 105 according to FIGS. 2a, 2c, 3a/3b. One possibility of variable element selection allows mounting-dependent optimization of the antenna geometry.

A symmetrical design (e.g., of the mechanics) of the bottom part U provides the local coil 106 may be used in a zero degree position for the right shoulder S (FIG. 3a) and in a 90 degree position for the left shoulder S (3b).

Dependent on the respective position (e.g., shoulder-coil 106 positioned on the left or right shoulder of the patient), certain elements may also be added or omitted (e.g., not connected/read out). This is advantageous, since the certain elements cover either the cranial part or the lateral part of the shoulder (e.g., by mechanical symmetry of the local coil 106 for the zero degree position and the 90 degree position). The top part elements K1, K2 cover, for example, exactly/roughly the same region in the process. The loop and/or butterfly elements on the electronic output device (e.g., including 67, 115,117) of the shoulder coil 106 and/or the MRT device 101 are connected depending on the position of the shoulder coil 106. This allows mounting-dependent optimization of the antenna geometry.

In FIGS. 2a, 2b, 2c, 3a, 3b, two movable top part elements (e.g., hinged elements) K1, K2 that may be laid one on top of the other, for example, and are in the form of lugs are provided on the fixed bottom part U so as to be movable relative thereto (e.g., hingeable) in the direction of arrows B1, B2. These top part elements K1, K2 in the form of lugs form a top part of the shoulder coil 106 that may be flexibly molded to a shoulder S. By folding out the, for example, lug-like top part elements K1, K2, the shoulder local coil 106 is accessible (from above) from the y direction. This allows easy access for the patient 105.

Flexible coil-antennae elements A1, A2, A3 in one or both respective lug-like hinged elements K1, K2, are arranged, for example, such that a triangular arrangement of coils A1-A3 that are read out/connected at one instant results (FIG. 2c).

FIG. 2c shows, by way of example, a hinged element K1 of a shoulder coil with coils (e.g., coil elements or antennae below) A1, A2, A3, A4, A5, A6. In the position of the shoulder coil S shown (in FIG. 2b, 2c), on the left shoulder S of the patient 105, the coils A1, A2, A3 are not connected to the electronic output device (e.g., including elements 67, 115, 117) of the coil and/or the MRT device, and the coils A4, A5, A6 are not connected to the electronic output device (e.g., including elements 67, 115, 117) of the shoulder coil 106 and/or the MRT device. In a position, which is not shown enlarged, of the shoulder coil S, on the right shoulder S of the patient 105, the coils A4, A5, A6 are connected to the electronic output device (e.g., including elements 67, 115,117) of the coil and/or the MRT device, and the coils A1, A2, A3 are not connected to the electronic output device (e.g., including elements 67, 115, 117) of the shoulder coil 106 and/or the MRT device.

This also allows great variability in the overlapping region of the lug-like top part elements K1, K2 without unnecessarily losing SNR due to coupling of individual antennae elements to each other of necessity. The mechanical bordering E (e.g., of the outer edge of the lugs made of, for example, plastic, in which the coils A1 of a hinged element K1 are located) of the flexible elements may be greater than the antennae elements A1-A6 to allow sufficient space for fixing options (e.g., Velcro® strips (FIG. 2b)). For example, a Velcro® strip on a top part element may be stuck to a Velcro® strip on another top part element to fix both of the top part elements in a position (y) above the shoulder (FIG. 2a).

According to FIGS. 3a and 3b, a cable outlet KA of the shoulder local coil 106 is located (e.g., in the center and/or axis of symmetry SY of the bottom part U or another part of the shoulder local coil 106), so the cable may be guided (e.g., from connecting cables for connection of the shoulder coil direct or via a splitter on the examination table to an MRT evaluator 168/117) from the cable outlet KA of the shoulder coil 106 to a connector field of an MRT. The cable may be guided both in the 0 degree position (FIG. 3a; shoulder coil on the right shoulder of the patient) and in the 90 degree position (FIG. 3b; shoulder coil on the left shoulder of the patient) of the shoulder-coil 106.

An illustrated pivot point D shows a point the shoulder-coil 106 may be rotated from the 0 degree position (FIG. 3a; shoulder coil on the right shoulder of the patient) into the 90 degree position (FIG. 3b; shoulder coil on the left shoulder of the patient) (e.g., before a patient lies on the shoulder-coil; the shoulder coil is pushed on the examination table from the position of the right shoulder to the position of the left shoulder).

The shoulder coil may be adjustable due to the flexible elements in the top part in the case of a symmetrical mechanical design of the bottom part. A symmetrical mechanical design and a mounting-dependent element selection may allow the use of the local coil 106 on the left and right shoulders. For comfort and advantageous workflow, the patient may position himself or herself from above in the shoulder coil 106. The configuration permits a shoulder coil 106 with partially flexible molding to the patient, handling of both shoulders using the same mechanism and mounting-dependent geometry, and an integrated workflow.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A shoulder coil for a magnetic resonance imaging device, the shoulder coil comprising:
   a bottom part; and
   at least two top part elements that are directly connected to the bottom part and are moveable relative to the bottom part, at least one coil being located in each top part element of the at least two top part elements,
   wherein two top part elements of the at least two top part elements are hingedly openable and closeable relative to the bottom part in different directions that are approximately perpendicular to one another, the two top part elements being closeable, such that the two top part elements are positioned with one of the two top part elements on top of the other of the two top part elements.

2. The shoulder coil as claimed in claim 1, wherein the bottom part is configured such that during magnetic resonance tomography (MRT) imaging, the bottom part is located under a patient, on an examination table, or under the patient and on the examination table.

3. The shoulder coil as claimed in claim 1, wherein a top part element of the at least two top part elements is hingeable in a direction from next to a shoulder to be examined into a position partially or completely above the shoulder.

4. The shoulder coil as claimed in claim 3, wherein another top part element of the at least two top part elements is hingeable in a direction from next to the shoulder to be examined into a position partially or completely above the shoulder.

5. The shoulder coil as claimed in claim 1, wherein a top part element of the at least two top part elements is hingeable in a direction from laterally, cranially, or laterally and cranially next to a shoulder to be examined into a position partially or completely above the shoulder.

6. The shoulder coil as claimed in claim 1, wherein at least one top part element of the at least two top part elements includes a plurality of coils.

7. The shoulder coil as claimed in claim 1, wherein at least one top part element of the at least two top part elements includes a plurality of coils,
   wherein first coils of the plurality of coils are connectable to an electronic output device of the shoulder coil, a magnetic resonance tomography (MRT) device, or the electronic output device and the MRT device, and
   wherein second coils of the plurality of coils are not connected to the electronic output device, the MRT device, or the electronic output device and the MRT device when the first coils are connected to the electronic output device, the MRT device, or the electronic output device and the MRT device.

8. The shoulder coil as claimed in claim 1, wherein at least one top part element of the at least two top part elements is a hinged element that is hingeable relative to the bottom part.

9. The shoulder coil as claimed in claim 1, wherein the bottom part has a mirror-symmetrical design.

10. The shoulder coil as claimed in claim 9, wherein the mirror-symmetrical design is configured to allow use of the bottom part for a right shoulder and a left shoulder.

11. The shoulder coil as claimed in claim 10, wherein the mirror-symmetrical design is configured to allow use of the bottom part for the right shoulder at a zero degree position and for the left shoulder at a ninety degree position.

12. The shoulder coil as claimed in claim 1, wherein the two movable top part elements are placeable on each other, and
   wherein the two moveable top part elements are arranged on the bottom part so as to be movable with respect to the bottom part.

13. The shoulder coil as claimed in claim 1, further comprising a cable outlet, wherein the cable outlet is located in a center of the shoulder coil, on an axis of symmetry of the shoulder coil, or in the center of and on the axis of symmetry of the shoulder coil.

14. The shoulder coil as claimed in claim 1, wherein top part elements of the at least two top part elements are arranged on the bottom part so as to be hinged relative to the bottom part by at least 90 degrees.

15. The shoulder coil as claimed in claim 14, wherein the top part elements are arranged on the bottom part so as to be hinged relative to the bottom part by more than 150 degrees.

16. The shoulder coil as claimed in claim 14, wherein the top part elements are arranged on the bottom part so as to be hinged relative to the bottom part by at least 180 degrees.

* * * * *